United States Patent [19]

Oude Alink

[11] 4,447,606

[45] May 8, 1984

[54] HYDROXY AND HYDROPEROXY TETRAHYDROPYRIMIDINES

[75] Inventor: Bernardus A. Oude Alink, St. Louis, Mo.

[73] Assignee: Petrolite Corporation, St. Louis, Mo.

[21] Appl. No.: 28,149

[22] Filed: Apr. 9, 1979

[51] Int. Cl.³ ............................................ C07D 239/72
[52] U.S. Cl. .................................................... 544/231
[58] Field of Search .............................. 544/231, 298

[56] References Cited

U.S. PATENT DOCUMENTS 3,041,338  6/1962  Phillips ................................ 544/298
3,904,625  9/1975  Alink .................................... 544/231

OTHER PUBLICATIONS

Kirk–Othmer, Encyclopedia of Chemical Technology, 2nd Ed., vol. 6 (1965) pp. 289–291.

Primary Examiner—Paul M. Coughlan, Jr.
Attorney, Agent, or Firm—Sidney B. Ring; Hyman F. Glass; Leon Zitver

[57] ABSTRACT

This invention relates to 5-hydroperoxy and/or 5-hydroxy derivatives of 2,2,4,4-dipentamethylene 5,6-tetramethylene 2,3,4,5-tetrahydropyrimidines; and to the preparation thereof. The compounds of this invention have utility as corrosion inhibitors.

5 Claims, No Drawings

HYDROXY AND HYDROPEROXY TETRAHYDROPYRIMIDINES

This invention relates to substituted hydroperoxy tetrahydropyrimidines and substituted hydroxy tetrahydropyrimidines, and the preparation and uses thereof.

Tetrahydropyrimidines employed as starting materials in the invention are derived from cyclohexanones such as described in U.S. Pat. No. 4,145,545 issued Mar. 20, 1979. Addition of oxygen to a 2,2,4,4-dipentamethylene 5,6-tetramethylene 2,3,4,5-tetrahydropyrimidine results in an oxidation reaction with insertion of the oxygen molecule in the $C_5$—H bond according to the following equation:

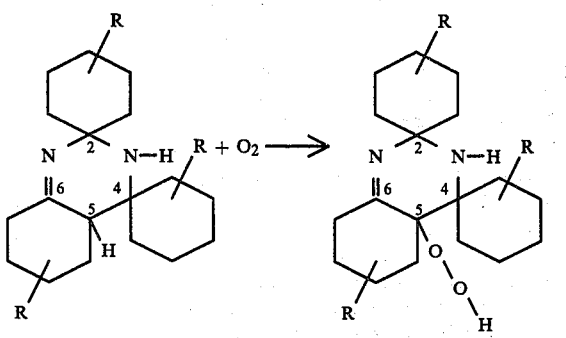

The hydroperoxy products are stable products which can be isolated. If desired, the oxidation is usually carried out in a solvent and any solvent which does not interfere with the reaction product or starting material can be used. Reaction temperature is ambient but lower or higher temperatures may be used.

In the second reaction the hydroperoxide is deoxygenated to the corresponding alcohol according to the following reaction:

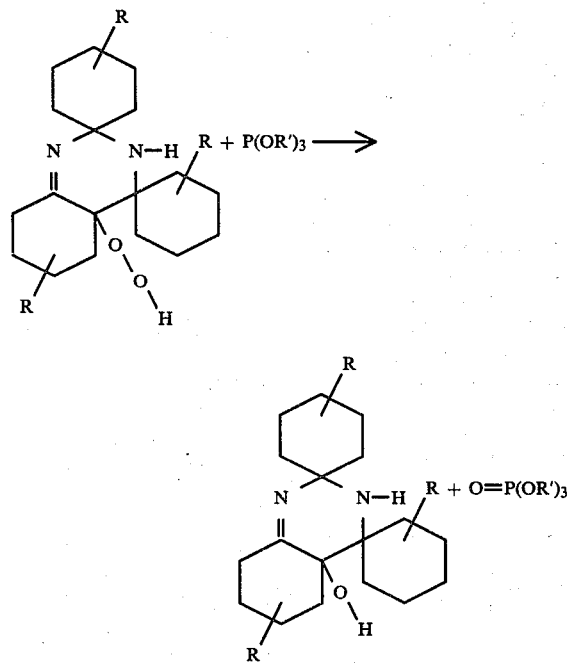

The deoxygenation reaction is carried out with a trialkyl (or triaryl) phosphite.

If desired, a solvent may be employed at ambient temperature but lower or higher temperatures can be used.

The two reactions may be combined and carried out as a one pot reaction by the addition of oxygen (or air) to a mixture of 2,2,4,4-dipentamethylene 5,6-tetramethylene 2,3,4,5-tetrahydropyrimidine and trialkyl (or triaryl phosphite) according to the following reaction:

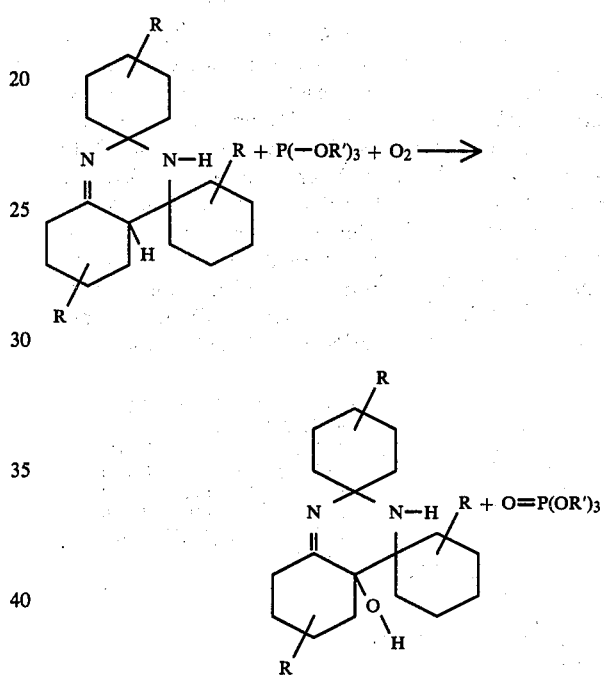

The following examples are presented for purposes of illustration and not of limitation.

EXAMPLE 1

2,2,4,4-Dipentamethylene 5,6-tetramethylene 2,3,4,5-tetrahydropyrimidine

A mixture of 294 grams of cyclohexanone and 5 grams of ammonium chloride was placed in a pressure reactor. Over a ¾ hour period 38.8 grams of ammonia gas was added. After the addition was complexed, the mixture was stirred for 5 hours at ambient temperature. The product was taken up in toluene and the aqueous phase which separated was discarded. The toluene solution was evaporated under diminished pressure to yield 268 grams of 2,2,4,4-dipentamethylene 5,6-tetramethylene 2,3,4,5-tetrahydropyrimidine, infrared spectrum 6.02μ (C=N) and 3.05μ (N—H), $C^{13}$ nuclear magnetic resonance spectrum, solvent $CDCL_3$, ref. TMS:

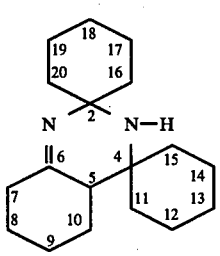

70.11 (2); 50.16 (4); 45.69 (5); 169.38 (6); 42.43 (7); 29.30 (8); 26.38 (9); 29.30 (10); 40.61 (11) 21.90*(12); 26.38 (13); 21.64*(14) 35.54 (15); 38.53 (16); 22.55*(17) 26.38 (18); 22.55*(19); 38.53 (20)

*values may be interchanged.

EXAMPLE 2

9,13,18-Trimethyl 2,2,4,4-dipentamethylene-5,6-tetramethylene 2,3,4,5-tetrahydropyrimidine A mixture of 75 grams of 4-methylcyclohexanone, 6.1 grams of ammonium chloride and 300 grams of toluene were placed in a pressure reactor. To the mixture was added with stirring 16.2 grams of ammonia gas over a 15 minute period. After the addition was completed, the mixture was stirred for 20 hours. The aqueous layer was removed and the toluene layer evaporated under diminished pressure to yield 66 grams of 9,13,18-trimethyl 2,2,4,4-dipentamethylene 5,6-tetramethylene 2,3,4,5-tetrahydropyrimidine, infrared spectrum 6.01μ (C=N), 3.08μ (N—H), $C^{13}$ nuclear magnetic resonance spectrum, solvent CDCl$_3$, reference T.M.S., δ in ppm.

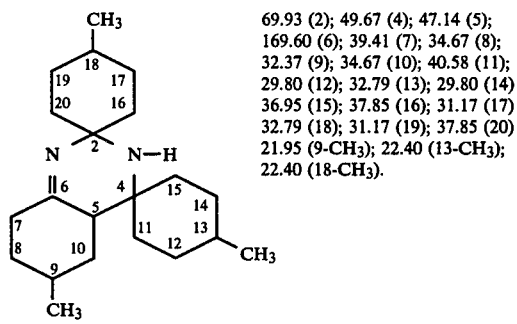

69.93 (2); 49.67 (4); 47.14 (5); 169.60 (6); 39.41 (7); 34.67 (8); 32.37 (9); 34.67 (10); 40.58 (11); 29.80 (12); 32.79 (13); 29.80 (14) 36.95 (15); 37.85 (16); 31.17 (17) 32.79 (18); 31.17 (19); 37.85 (20) 21.95 (9-CH$_3$); 22.40 (13-CH$_3$); 22.40 (18-CH$_3$).

EXAMPLE 3

2,2,4,4-Dipentamethylene 5,6-tetramethylene 5-hydroperoxy 2,3,4,5-tetrahydropyrimidine Into a mixture of 50 grams of 2,2,4,4-dipentamethylene 5,6-tetramethylene 2,3,4,5-tetrahydropyrimidine (prepared as described in example 1) and 1000 cc of hexanes air was introduced for 19 hours. The resulting hexane insoluble white solid which precipitated was isolated and dried to yield 43 grams of 2,2,4,4-dipentamethylen 5,6-tetramethylene-5-hydroperoxy-2,3,4,5-tetrahydropyrimidine, m.p. 119°-120° C. infrared spectrum (KBr) 2.94μ (N—H), 3.01μ (O—H) and 6.05μ (C=N).

Anal. Calc.ed for $C_{18}H_{30}N_2O_2$: C, 70.59; H, 9.80; N, 9.15. Found: C, 70.99; H, 9.84; N, 9.11.

In the same manner as described above, introduction of oxygen into a solution of 2,2,4,4-dipentamethylene 5,6-tetramethylene 2,3,4,5-tetrahydropyrimidine in toluene yielded the corresponding 5-hydroperoxy tetrahydropyrimidine:

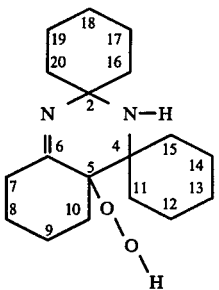

EXAMPLE 4

2,2,4,4-Dipentamethylene 5,6-tetramethylene-5-hydroxy 2,3,4,5-tetrahydropyrimidine To a mixture of 15.3 grams of 2,2,4,4-dipentamethylene 5,6-tetramethylene 5-hydroperoxy 2,3,4,5-tetrahydropyrimidine (prepared as described in example 3) in 500 cc of toluene was added a sample of 8.4 grams of triethylphosphite. The mixture was cooled and stirred for three hours. An additional 500 cc of toluene was added and the resulting toluene solution was washed three times with a 10% aqueous sodium hydroxide solution and three times with water. The toluene solution was evaporated under diminished pressure to yield 14 grams of 2,2,4,4-dipentamethylene 5,6-tetramethylene 5-hydroxy 2,3,4,5-tetrahydropyrimidine, m.p. 94°-95° C. (crystallized from ethanol-water), infrared spectrum (KBr), 3.02μ (O—H) and 6.10μ (C=N), $^{13}$C nuclear magnetic resonance spectrum, solvent CDCl$_3$, reference T.M.S., δ in ppm:

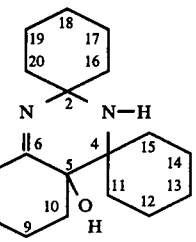

70.21 (2); 55.19 (4); 70.04 (5); 167.65 (6); 34.98 (7); 26.54*(8); 22.89*(9); 30.92 (10); 31.41 (11); 21.02*(12); 25.73*(13); 21.18(14); 42.61 (15); 37.82 (16); 21.43*(17) 25.32*(18); 22.56*(19); 37.82*

*values may be interchanged.

Anal. Calc.ed for $C_{18}H_{30}N_2O$: C, 74.48, H, 10.35; N, 9.66. Found: C, 74.32; H, 10.77; N, 9.33.

The same product as described in example 4 may be prepared by introduction of air (or oxygen) into a mixture of 2,2,4,4-dipentamethylene 5,6-tetramethylene 2,3,4,5-tetrahydropyrimidine and triethylphosphite without isolation of 2,2,4,4-dipentamethylene 5,6-tetramethylene 5-hydroperoxy 2,3,4,5-tetrahydropyrimidine. If desired the use of triethylphosphite may be substituted for a trialkyl or triarylphosphite.

The following hydroperoxy and hydroxy tetrahydropyrimidines were prepared according to the method described in examples 3 and 4.

| Ex. No. | Starting material | Product |
| --- | --- | --- |
| 5 | Product of example 2 | 9,13,18-Trimethyl 5-hydroperoxy 2,2,4,4-dipentamethylene 5,6-tetramethylene 2,3,4,5-tetrahydropyrimidine |

-continued

| Ex. No. | Starting material | Product |
|---|---|---|
| 6 | 9,13,18-Trimethyl 5-hydroperoxy 2,2,4,4-dipentamethylene 5,6-tetramethylene 2,3,4,5-tetrahydropyrimidine | 9,13,18-Trimethyl 5-hydroxy 2,2,4,4-dipentamethylene 5,6-tetramethylene 2,3,4,5-tetrahydropyrimidine |
| 7 | 8,12,17-Trimethyl 2,2,4,4-dipentamethylene 5,6-tetramethylene 2,3,4,5-tetrahydropyrimidine | 8,12,17-Trimethyl 2,2,4,4-dipentamethylene 5-hydroperoxy 5,6-tetramethylene 2,3,4,5-tetrahydropyrimidine |
| 8 | 8,12,17-Trimethyl 2,2,4,4-dipentamethylene 5-hydroperoxy 5,6-tetramethylene 2,3,4,5-tetrahydropyrimidine | 8,12,17-Trimethyl 2,2,4,4-dipentamethylene 5-hydroxy 5,6-tetramethylene 2,3,4,5-tetrahydropyrimidine |
| 9 | 9,13,18-Triisopropyl 2,2,4,4-dipentamethylene 5,6-tetramethylene 2,3,4,5-tetrahydropyrimidine | 9,13,18-Triisopropyl 5-hydroxy 2,2,4,4-dipentamethylene 5,6-tetramethylene 2,3,4,5-tetrahydropyrimidine |

The compositions of this invention have many uses including their use as corrosion inhibitors. For example, the products of Examples 4, 6, and 8 are effective corrosion inhibitors.

I claim:

1. 5-hydroperoxy, 5-hydroxy or mixtures thereof derivatives of 2,2,4,4-dipentamethylene 5,6-tetramethylene 2,3,4,5-tetrahydropyrimidines.

2. A process of preparing the 5-hydroxy tetrahydropyrimidines of claim 1 which comprises reacting the 5-hydroperoxy tetrahydropyrimidines of claim 1 with trialkyl (or triaryl) phosphites.

3. A process of preparing the 5-hydroxy tetrahydropyrimidines of claim 1 which comprises reacting 2,2,4,4-dipentamethylene 5,6-tetramethylene 2,3,4,5-tetrahydropyrimidines with oxygen in the presence of trialkyl (or triaryl) phosphites.

4. The tetrahydropyrimidine of claim 1 which is the 5-hydroperoxy derivative of a 2,2,4,4-dipentamethylene 5,6-tetramethylene 2,3,4,5-tetrahydropyrimidine.

5. The tetrahydropyrimidine of claim 1 which is the 5-hydroxy derivative of a 2,2,4,4-dipentamethylene 5,6-tetramethylene 2,3,4,5-tetrahydropyrimidine.

* * * * *